United States Patent [19]

Neef et al.

[11] Patent Number: 4,780,461
[45] Date of Patent: Oct. 25, 1988

[54] 13α-ALKYL-GONANES, THEIR PRODUCTION, AND PHARMACEUTICAL PREPARATIONS CONTAINING SAME

[75] Inventors: Günter Neef; Rudolf Wiechert; Sybille Beier; Walter Elger; David Henderson, all of Berlin, Fed. Rep. of Germany

[73] Assignee: Schering Aktiengesellschaft, Berlin and Bergkamen, Fed. Rep. of Germany

[21] Appl. No.: 810,148

[22] Filed: Dec. 18, 1985

Related U.S. Application Data

[63] Continuation-in-part of Ser. No. 621,308, Jun. 15, 1984, abandoned.

[30] Foreign Application Priority Data

Jun. 15, 1983 [DE] Fed. Rep. of Germany ....... 3321826
Apr. 4, 1984 [DE] Fed. Rep. of Germany ....... 3413036
Dec. 18, 1984 [DE] Fed. Rep. of Germany ....... 3446661

[51] Int. Cl.$^4$ .......................... A61K 31/56; C07J 1/00
[52] U.S. Cl. ............................. 514/179; 260/397.45; 260/397.5; 514/182; 540/34; 540/36
[58] Field of Search ................ 260/397.45; 514/179, 514/182; 540/34, 36

[56] References Cited

U.S. PATENT DOCUMENTS 4,233,296 11/1980 Teutsch et al. .

OTHER PUBLICATIONS

Chemical Abstracts, vol. 90, 90:104208y, 1979, pp. 619–620.
Neef et al., Tetrahedron Letters, vol. 25, No. 32, pp. 3425–3428 (1984).
Neef et al., Steroids, (1985).
Berichte der Deutschen Chemischen Gesellschaft, Nr. 7, 1941, pp. 1308, 1312.

Primary Examiner—Leonard Schenkman
Assistant Examiner—Joseph A. Lipovsky
Attorney, Agent, or Firm—Millen & White

[57] ABSTRACT

13α-alkylgonanes of formula I

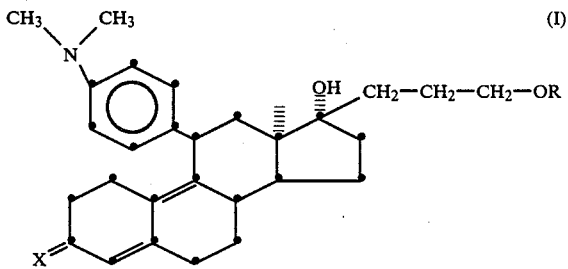

where
R is an acyl radical with as many as 10 C-atoms, and
X is an oxygen atom or the grouping N—OH, have a strong antigestagenic effect and can be used for postcoital fertility control.

41 Claims, No Drawings

13α-ALKYL-GONANES, THEIR PRODUCTION, AND PHARMACEUTICAL PREPARATIONS CONTAINING SAME

CROSS REFERENCE TO RELATED APPLICATION

This application is a continuation-in-part of U.S. Ser. No. 621,308 of June 15, 1984, now abandoned, which is entirely incorporated by reference herein.

BACKGROUND OF THE INVENTION

This invention relates to new 13α-alkyl-17β-(3-acyloxy-propyl)-gonanes, a process for their manufacture and pharmaceutical preparations containing them. 13α-alkyl-17β-(3-hydroxypropyl)-4,9-gonadiene-3-ones are described in European Patent Application No. 84730062.1, corresponding to U.S. Ser. No. 621,308 above. These compounds have a strong affinity for gestagen receptors, without themselves having any gestagenic activity. They are competitive antagonists of progesterone (antigestagens) and are suitable for inducing abortions since they displace from the receptor the progesterone necessary for maintenance of pregnancy. The compounds are thus valuable and of interest from the point of view of their use for postcoital (p.c.) control of fertility.

SUMMARY OF THE INVENTION

It is an object of this invention to provide such compounds which have advantageous properties.

Upon further study of the specification and appended claims, further objects and advantages of this invention will become apparent to those skilled in the art.

These objects have been achieved by providing 13α-alkylgonanes of formula I

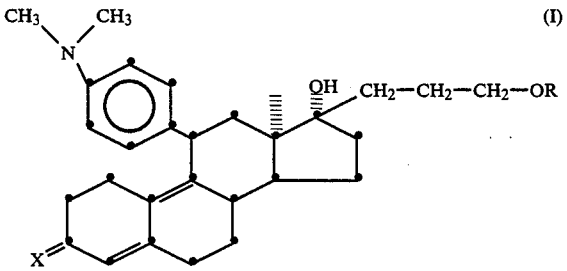

where
R is an acyl radical of up to 10 C-atoms and
X is an oxygen atom or the grouping N~OH,
as well as the corresponding pharmaceutical compositions and methods of use.

DETAILED DISCUSSION

It has now been found that the bio-availability of the mentioned prior components can, surprisingly, be considerably surpassed by providing 13α-alkyl-17β-(3-acyloxypropyl)-gonanes of general formula I. In comparison to the previously known 13α-alkyl-17β-(3-hydroxypropyl)-4,9-gonadiene-3-ones they display a prolonged duration of effectiveness for the mentioned uses with the same or greater effect. The new compounds also possess excellent crystallization properties which is another advantage. The preparation of the pure active substance is thus much less difficult in their case than in the case of 13-alkyl-17-(3-hydroxypropyl)-4,9-gonadiene-3-ones.

Furthermore, they possess excellent chemical stability. They can be stored with no difficulty for a long period of time at room temperature without decomposing.

The acyl radical R in general formula I can contain as many as 10 C-atoms. Non-limiting examples of suitable acyl radicals are, for example, formyl, acetyl, propionyl, butyryl, isobutyryl, valeryl, isovaleryl, glycoloyl, cyclopentylacetyl, mono-, di-, or trichloroacetyl, benzoyl, trifluoromethylbenzoyl and nicotinoyl radicals; preferred are the acetyl and benzoyl radicals.

R generally is derived from a $C_{1-10}$-hydrocarbon-based carboxylic acid which may be aliphatic or aromatic and acyclic or cyclic. Optional substituents for such acyl groups include halo, mono-, di-, or tri-halo(F or Cl especially)-alkyl(methyl especially), hydroxy, alkyl, cycloalkyl, etc. The cyclic moieties can also include a hetero atom, e.g., O, N or S. All of the mentioned possibilities are equivalents of the generically described $C_{1-10}$-hydrocarbon-based carboxylic acids. Many other equivalents of such acyl groups are well-known in the steroid field and are contemplated for use herein. See, e.g., U.S. Pat. No. 4,196,204 which disclosure is incorporated by reference herein.

X can be oxygen or the group N OH, with the hydroxyimino radical being in the syn or anti-position.

The compounds of formula I in accordance with this invention are prepared in accordance with generally known methods, e.g., by reacting a compound of formula II

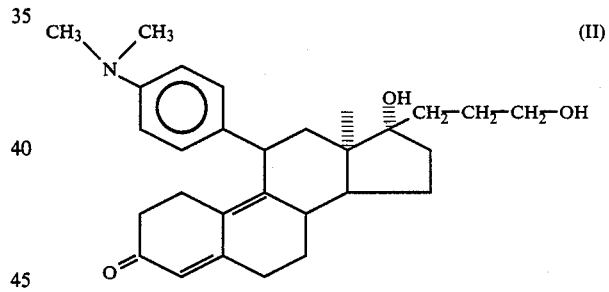

with an acid chloride or acid anhydride of general formula III or IV, respectively,

where
R is as defined above, in the presence of a base at temperatures between about 0° and 60° C. and, if desired subsequently reacting the product with hydroxylamine hydrochloride in the presence of a tertiary amine at temperatures between about −20° and +40° C.

The preferred bases for esterification are tertiary amines such as pyridine. The preferred tertiary amine for use in the conversion for the preparation of oximes is pyridine. Further suitable tertiary bases include, for example, trimethylamine, triethylamine, N,N-dimethylamino pyridine, 1,5-diazabicyclo[4.3.0]nonene-5 (DBN) and 1,5-diazabicyclo[5.4.0]undecene-5 (DBU).

The starting materials of Formula II are known and/or preparable by conventional methods from known or readily preparable starting materials. See, e.g., U.S. Ser. No. 621,308. The 13-alkylgonanes of general formula I can be used in the form of pharmaceutical preparations for administration to mammals, including humans, e.g., for the purposes mentioned above with respect to U.S. Ser. No. 621,308, which entire disclosure regarding formulation and use of the compounds is applicable here unless indicated otherwise. The preparations can be manufactured by the methods generally known in galenics by mixing with organic or inorganic inert carrier material suitable for enteral, percutaneous or parenteral application.

For humans the dosage of the active ingredients in accordance with the invention is approximately 10 to 1000 mg per day, preferably 25–200 mg/day to induce abortions or trigger menstruation analogous to the known agent RU486. Typical unit dosages are 10–100 mg.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

A solution of 2.4 g of 11β-(4-dimethylaminophenyl)-17α-hydroxy-13α-methyl-17β(3-hydroxypropyl)-4,9-gonadiene-3-one in 7 ml of pyridine and 14 ml of acetanhydride is stirred for 14 hours at 25° C. This mixture is then poured into warm water (100 ml) at a temperature of approximately 50° C., stirred for 15 minutes and the cooled emulsion extracted with methylene chloride. The methylene chloride phase is washed neutral with NaHCO$_3$ solution, dried over Na$_2$SO$_4$ and concentrated. Crystallization of the crude product from ethylacetate/diisopropyl ether yields 2.24 g of 17β-(3-acetoxypropyl)-11β-(4-dimethylaminophenyl)-17α-hydroxy-13α-methyl-4,9-gonadiene-3-one with a melting point of 162°–164° C.

[α]$_D^{25}$+436.5° (CHCl$_3$, c=0.515).

EXAMPLE 2

0.36 ml of benzoyl chloride in 4 ml of methylene chloride are dripped, ice-cooled, into a solution of 700 mg of 11-(4-dimethylaminophenyl)-17α-hydroxy-13α-methyl-17β-(3-hydroxypropyl)-4,9-gonadiene-3-one. The mixture is stirred for 60 minutes at +5° C., then poured into saturated HaHCO$_3$ solution and extracted with ethyl acetate. Crystallization of the crude product from hexane/diisopropyl ether yields 630 mg of 17β-(3-benzoyloxypropyl)-11β-(4-dimethylaminophenyl)-17α-hydroxy-13α-methyl-4,9-gonadiene-3-one with a melting point of 114°–116° C.

EXAMPLE 3

A solution of 630 mg of 17β-(3-acetoxypropyl)-11β-(4-dimethylaminophenyl)-17α-hydroxy-13α-methyl-4,9-gonadiene-3-one in 10 ml of pyridine is stirred for 1.5 hours at 0° C. after the addition of 600 mg of hydroxylamine hydrochloride. The mixture is subsequently poured into a mixture of ice water and saturated NH$_4$Cl solution and extracted with ethyl acetate. After chromatography on silica gel with hexane/ethyl acetate 410 mg of 17β-(3-acetoxypropyl)-11β-(4-dimethyl-aminophenyl)-17α-hydroxy-13α-methyl-4,9-gonadiene-3-one-anti-oxime are obtained with a melting point of 201°–204° C.

UV (MeOH): $\lambda_{max}$=288 nm ($\epsilon$=27,400).

EXAMPLE 4

Composition of a tablet with the preferred agent

| 11β-(4-dimethylaminophenyl)-17α-hydroxy-13α-methyl-17β-(3-hydroxypropyl)-4,9-gonadiene-3-one for oral application | |
|---|---|
| 10.0 mg | 11β-(4-dimethylaminophenyl)-17α-hydroxy-13α-methyl-17β-(3-hydroxypropyl)-4,9-gonadiene-3-one |
| 140.0 mg | lactose |
| 69.5 mg | corn starch |
| 2.5 mg | polyvinlpyrrolidone 25 |
| 2.0 mg | "Aerosil" |
| 0.5 mg | magnesium stearate |
| 225.0 mg | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 13α-alkylgonane of the formula

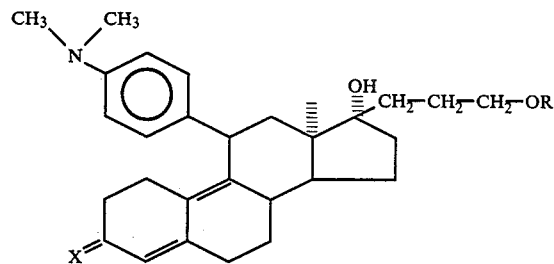

wherein

R is an acyl radical of a C$_{1-10}$-hydrocarbon carboxylic acid, and

X is oxygen or NOH.

2. A compound of claim 1, wherein X is oxygen.

3. A compound of claim 1, wherein X is NOH.

4. A compound of claim 1, wherein R is C$_{1-5}$-alkanoyl or benzoyl.

5. A compound of claim 1, wherein R is acetyl or benzoyl.

6. 17β-(3-acetoxypropyl)-11β-(4-dimethylaminophenyl)-17α-hydroxy-13α-methyl-4,9-gonadiene-3-one, a compound of claim 1.

7. 17β-(3-benxoyloxypropyl)-11β-(4-dimethylaminophenyl)-17α-hydroxy-13α-methyl-4,9-gonadiene-3-one, a compound of claim 1.

8. 17β-(3-acetoxypropyl)-11β-(4-dimethylaminophenyl)-17α-hydroxy-13α-methyl-4,9-gonadiene-3-one-anti-oxime, a compound of claim 1.

9. A pharmaceutical composition comprising a labor inducing amount of a compound of claim 1 and a pharmaceutically acceptable carrier.

10. A composition of claim 9, wherein the amount of said compound is 10-100 mg.

11. A method of inducing an abortion comprising administering an effective amount of a compound of claim 1 to a patient in need thereof.

12. A method of triggering menstruation comprising administering an effective amount of a compound of claim 1 to a patient in need thereof.

13. A method of achieving an antigestagenic effect comprising administering an effective amount of a compound of claim 1 to a patient in need thereof.

14. 11β-(4-dimethylaminophenyl)-17α-hydroxy-17β-(3-hydroxypropyl)-13α-methyl-4,9-gonadien-3-one, a compound of claim 1.

15. A pharmaceutical composition comprising an antigestagenically effective amount of the compound of claim 14 in admixture with a pharmaceutically acceptable carrier.

16. A method of achieving an antigestagenic effect in a patient in need of such treatment comprising administering to the patient an effective amount of a compound of claim 14.

17. A method of triggering an abortion comprising administering an effective amount of a compound of claim 14 to a patient in need thereof.

18. 13α-Alkyl gonanes of the formula

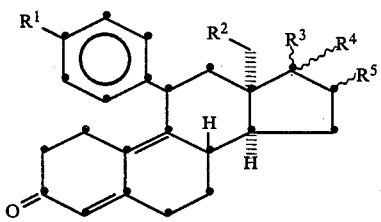

wherein
R¹ is

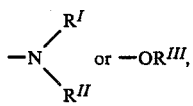

wherein $R^I$ and $R^{II}$ each are hydrogen or alkyl of 1-4 carbon atoms, or $R^I$ and $R^{II}$ collectively with N are a saturated 5- or 6-membered monoheterocyclic ring or a corresponding ring containing O, N or S as a further hetero ring atom, the corresponding tertiary N-oxides of each of the foregoing, and the acid addition salts thereof, and $R^{III}$ is methyl, ethyl, propyl, methoxyphenyl, allyl or β-dimethylaminoethyl;

R² is hydrogen, methyl or ethyl;

R³ is —(CH₂)ₙ—CH₃ wherein n=0-4, —(CH₂)ₙ—CH₂—O(S)$R^{IV}$ wherein n=0-4 and $R^{IV}$ is hydrogen or alkyl of 1-4 carbon atoms, —CH═CH—(CH₂)ₙ—OR$^V$ wherein n=1-4 and R$^V$ is hydrogen, alkyl or alkanoyl of respectively 1-4 carbon atoms, —C≡C—X wherein X is hydrogen, alkyl of 1-4 carbon atoms, or halogen, —(CH₂)ₙ—CH₂CN wherein n=0-3, or

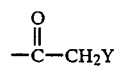

wherein Y is hydrogen or OR$^V$ wherein R$^V$ is as defined above;

R⁴ is hydroxy, alkoxy or alkanoyloxy each of 1-4 carbon atoms; or

R³ and R⁴ collectively are

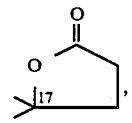

and

R⁵ is hydrogen or alkyl of 1-4 carbon atoms.

19. 11β-(4-Dimethylaminophenyl)-17α-ethynyl-17β-hydroxy-13α-methyl-4,9-gonadien-3-one and 11β-(4-dimethylaminophenyl)-17β-ethynyl-17α-hydroxy-13α-methyl-4,9-gonadien-3-one, compounds of claim 18.

20. 11β-(4-Dimethylaminophenyl)-17β-hydroxy-13α-methyl-17α-propynyl-4,9-gonadien-3-one and 11β-(4-dimethylaminophenyl)-17α-hydroxy-13α-methyl-17β-propynyl-4,9-gonadien-3-one, compounds of claim 18.

21. 11β-(4-Dimethylaminophenyl)-17α-hydroxy-13α-methyl-18,19-bisnor-4,9-pregnadiene-3,20-dione and 17α-acetoxy-11β-(4-dimethylaminophenyl)-13α-methyl-18,19-dinor-4,9-pregnadiene-3,20-dione, compounds of claim 18.

22. 11β-(4-Diethylaminophenyl)-17α-(3-hydroxypropyl)-17β-hydroxy-13α-methyl-4,9-gonadien-3-one and 11β-(4-diethylaminophenyl)-17β-(3-hydroxypropyl)-17α-hydroxy-13α-methyl-4,9-gonadien-3-one, compounds of claim 18.

23. 11β-(4-Dimethylaminophenyl)-17β-hydroxy-17α(3-hydroxypropyl)-13α-methyl-4,9-gonadien-3-one and 11β-(4-dimethylaminophenyl)-17α-hydroxy-17β-(3-hydroxypropyl)-13α-methyl-4,9-gonadien-3-one, compounds of claim 18.

24. 17β-Ethynyl-17α-hydroxy-11β-(4-methoxyphenyl)-13α-methyl-4,9-gonadien-3-one, a compound of claim 18.

25. 11β-(4-Dimethylaminophenyl)-17β-ethynyl-13α-ethyl-17α-hydroxy-4,9-gonadien-3-one and 17α-acetoxy-11β-(4-dimethylaminophenyl)-13α-ethyl-18,19-dinor-4,9-pregnadiene-3,20-dione, compounds of claim 18.

26. 11β-(4-Dimethylaminophenyl)-17α-hydroxy-17β-(3-hydroxy-1(Z)-propenyl)-13α-methyl-4,9-gonadien-3-one, a compound of claim 18.

27. 11β-(4-Dimethylaminophenyl)-17β-ethynyl-16β-ethyl-17α-hydroxy-13α-methyl-4,9-gonadien-3-one, a compound of claim 18.

28. 17β-Cyanomethyl-11β-(4-dimethylaminophenyl)-17α-hydroxy-13α-methyl-4,9-gonadien-3-one, a compound of claim 18.

29. A pharmaceutical composition comprising a labor inducing amount of a compound according to claim 18 in admixture with a pharmaceutically acceptable carrier.

30. A process which comprises the step of irradiating with ultraviolet light a compound of the formula

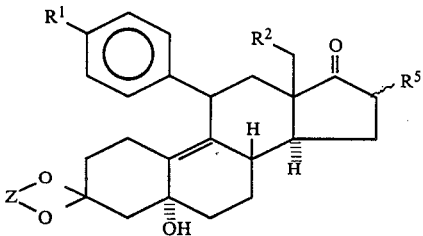

wherein R¹, R², and R⁵ have the values given in claim 1 and Z is ethylene or 2,2-dimethylpropylene, to produce a 13-episteroid of the formula

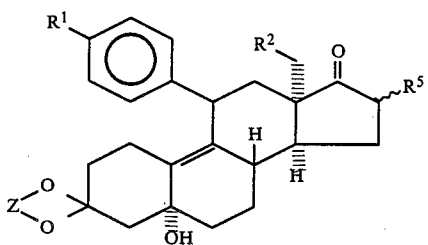

wherein R¹, R², R⁵ have the values given in claim 18 and Z is an ethylene or 2,2-dimethylpropylene.

31. A method of triggering an abortion comprising administering an effective amount of a compound of claim 18 to a patient in need thereof.

32. A compound of claim 18, wherein R¹ is OR$^{III}$ wherein R$^{III}$ is methyl, ethyl, propyl, methoxyphenyl or allyl.

33. A compound of claim 18, wherein R¹ is OR$^{III}$ wherein R$^{III}$ is methoxyphenyl or allyl.

34. A compound of claim 18, wherein R³ is —CH=CH—(CH$_2$)$_n$—OR$^V$.

35. A compound of claim 18, wherein R³ is —(CH$_2$)$_n$—CH$_2$CN.

36. A compound of claim 18, wherein R³ is —C≡C—X wherein X is halogen.

37. A compound of claim 18, wherein R³ and R⁴ together are

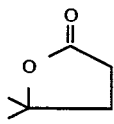

38. A compound of claim 18, wherein R³ is —(CH$_2$)$_n$—CH$_2$—O(S)R$^{IV}$.

39. A compound of claim 38, wherein O(S) is —S—.

40. A 13α-alkylgonane of the formula

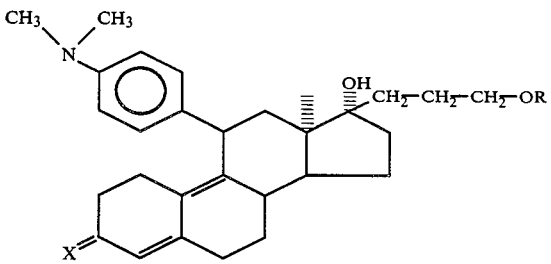

wherein
R is an acyl group of a C$_{1-10}$-hydrocarbon carboxylic acid or is glycoloyl, mono-, di- or tri-chloroacetyl, trifluoromethylbenzoyl or nicotinoyl, and
X is oxygen or NOH.

41. 13-Episteroids of the formula

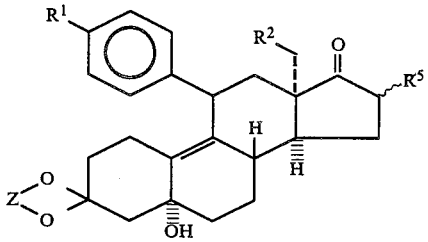

wherein
R¹ is

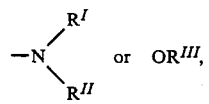

wherein R$^I$ and R$^{II}$ each are hydrogen or alkyl of 1-4 carbon atoms, or R$^I$ and R$^{II}$ collectively with N are a saturated 5- or 6-membered monoheterocyclic ring or a corresponding ring containing O, N or S as a further hetero ring atom, the corresponding tertiary N-oxides of each of the foregoing and the acid addition salts thereof, and R$^{III}$ is methyl, ethyl, propyl, methoxyphenyl, allyl or β-dimethylaminoethyl;
R² is hydrogen, methyl or ethyl;
R⁵ is hydrogen or alkyl of 1-4 carbon atoms; and
Z is an ethylene or 2,2-dimethylpropylene.

* * * * *

UNITED STATES PATENT AND TRADEMARK OFFICE
CERTIFICATE OF CORRECTION

PATENT NO. : 4,780,461

DATED : October 25, 1988

INVENTOR(S) : NEEF et al.

It is certified that error appears in the above-identified patent and that said Letters Patent is hereby corrected as shown below:

Column 5, claim 14, line 3, reads "compound of claim 1."

should read -- compound of claim 18. --

Signed and Sealed this

Thirtieth Day of June, 1992

*Attest:*

DOUGLAS B. COMER

*Attesting Officer*      *Acting Commissioner of Patents and Trademarks*